United States Patent [19]

Winkler et al.

[11] Patent Number: 5,384,261
[45] Date of Patent: Jan. 24, 1995

[54] VERY LARGE SCALE IMMOBILIZED POLYMER SYNTHESIS USING MECHANICALLY DIRECTED FLOW PATHS

[75] Inventors: James L. Winkler; Stephen P. A. Fodor; Christopher J. Buchko, all of Palo Alto; Debra A. Ross, Fremont; Lois Aldwin, San Mateo, all of Calif.

[73] Assignee: Affymax Technologies N.V., Curacao, Netherlands Antilles

[21] Appl. No.: 796,243

[22] Filed: Nov. 22, 1991

[51] Int. Cl.⁶ ............................................. G01N 33/543
[52] U.S. Cl. ................................... 436/518; 436/527; 436/531; 436/532; 436/501; 436/809; 436/807; 435/7.1; 435/968; 435/969; 435/970; 435/973; 530/334; 530/335; 530/337; 422/134; 422/149
[58] Field of Search ................... 436/518, 527-528, 436/530-532, 807, 809, 89, 116, 501; 530/333-337; 435/6, 7.1, 7.4, 7.92, 961, 968, 969, 970, 973, 975, 4; 422/131, 134, 149; 935/88

[56] References Cited

U.S. PATENT DOCUMENTS

| | | | |
|---|---|---|---|
| 3,848,998 | 11/1974 | Yonekura et al. | 430/271 X |
| 4,166,457 | 9/1979 | Jacobsen et al. | 128/639 |
| 4,392,362 | 7/1983 | Little | 62/514 R |
| 4,598,049 | 7/1986 | Zelinka et al. | 435/287 |
| 4,668,476 | 5/1987 | Bridgham et al. | 422/62 |
| 4,704,256 | 11/1987 | Hood et al. | 422/68 |
| 4,728,502 | 3/1988 | Hamill | 422/116 |
| 4,746,490 | 5/1988 | Saneii | 422/62 |
| 4,861,420 | 8/1989 | Knutti et al. | 156/633 |
| 4,861,866 | 8/1989 | Durrum et al. | 520/333 |
| 4,943,032 | 7/1990 | Zdeblick | 251/11 |
| 4,966,646 | 10/1990 | Zdeblick | 156/633 |
| 4,997,521 | 3/1991 | Howe et al. | 156/651 |
| 5,026,773 | 6/1991 | Steel | 525/54.11 |
| 5,037,882 | 8/1991 | Steel | 525/54.11 |
| 5,053,454 | 10/1991 | Judd | 525/54.11 |
| 5,100,626 | 3/1992 | Levin | 422/100 |
| 5,143,854 | 9/1992 | Pirrung et al. | 436/518 |
| 5,175,209 | 12/1992 | Beattie et al. | 525/54.11 |

FOREIGN PATENT DOCUMENTS

| | | | |
|---|---|---|---|
| 62-254034 | 11/1987 | Japan | G01N 1/28 |
| WO89/10977 | 11/1989 | WIPO . | |
| WO90/00626 | 1/1990 | WIPO | 530/333 |
| 9002605 | 3/1990 | WIPO | 530/334 |
| WO90/03382 | 4/1990 | WIPO . | |
| WO90/15070 | 12/1990 | WIPO | C07K 1/04 |
| WO91/07087 | 5/1991 | WIPO | 436/518 |

OTHER PUBLICATIONS

Sze, "Lithography" Chapter 7, *VLSI Technology*, McGraw-Hill Book Company, 1983, pp. 267–301.

Abbott et al., "Manipulation of the Wettability on Surfaces on the 0.1-to 1-Micrometer Scale Through Micromachining and Molecular Self-Assembly," *Science* (1992) 257:1380–1382.

Bhatia et al., "New Approach to Producing Patterned Biomolecular Assemblies," *J. Am. Chem. Soc.* (1992) 114:4432–4433.

Haridasan et al., "Peptide Synthesis Using Photolytically Cleavable 2-Nitrobenzyloxycarbonyl Protecting Group," *Proc. Indian Natl. Sci. Acad.* (1987) 53:717–728.

Frank et al., "Simultaneous Multiple Peptide Synthesis Under Continuous Flow Conditions on Cellulose Paper Discs as Segmental Solid Supports", Tetrahedron 44:6031–6040 (1988).

Knutti, "Silicon Microsystems as an Industry," presented at Microsystems 1990; Sep. 10–13, Berlin Germany.

Knutti, "Emerging Silicon Microstructures," Undated.

Knutti, "Advanced Silicon Microstructures," presented at ASICT Conference; Apr. 11, 1989; Toyohashi, Japan.

Fodor et al., *Science* (1991) 251:767–777.

Frank et al., *Nucleic Acids Research* (1983) 11:4365–4377.

Primary Examiner—Carol A. Spiegel
Attorney, Agent, or Firm—Kevin R. Kaster; Vern Norviel

[57] ABSTRACT

A method and device for forming large arrays of polymers on a substrate (401). According to a preferred aspect of the invention, the substrate is contacted by a channel block (407) having channels (409) therein. Selected reagents are flowed through the channels, the substrate is rotated by a rotating stage (403), and the process is repeated to form arrays of polymers on the substrate. The method may be combined with light-directed methodolgies.

14 Claims, 6 Drawing Sheets

VERY LARGE SCALE IMMOBILIZED POLYMER SYNTHESIS USING MECHANICALLY DIRECTED FLOW PATHS

BACKGROUND OF THE INVENTION

The present invention relates to the field of polymer synthesis. More specifically, in one embodiment the invention provides an improved method and system for synthesizing arrays of diverse polymer sequences. According to a specific aspect of the invention, a method of synthesizing diverse polymer sequences such as peptides or oligonucleotides is provided. The diverse polymer sequences may be used, for example, in screening studies for determination of binding affinity.

Methods of synthesizing desired polymer sequences such as peptide sequences are well known to those of skill in the art. For example, the so-called "Merrifield" solid-phase peptide synthesis has been in common use for several years and is described in Merrifield, *J. Am. Chem. Soc.* (1963) 85:2149–2154, incorporated herein by reference for all purposes. Solid-phase peptide synthesis techniques have been extended to provide for the synthesis of several peptide sequences on, for example, a number of "pins" as described in, for example, Geysen et. al., *J. Immun. Meth.* (1987) 102:259–274, also incorporated herein by reference for all purposes. Methods of synthesizing oligonucleotides are found in, for example, *Oligonucleotide Synthesis: A Practical Approach*, Gait, ed., IRL Press, Oxford (1984), incorporated herein by reference in its entirety for all purposes.

Such methods and devices have continued to be limited in the number of sequences which can be synthesized in a reasonable amount of time. For example, Geysen et. al. report in the above journal that it has taken approximately 3 years to synthesize 200,000 peptide sequences. Such methods have continued to produce fewer peptide sequences for study than are often desired.

Accordingly, improved methods of forming large arrays of peptides, oligonucleotides, and other polymer sequences in a short period of time have been devised. Of particular note, Pirrung et. al., PCT Application No. WO 90/15070 and U.S. application Ser. No. 07/624,120, both incorporated herein by reference, disclose methods of forming vast arrays of peptides and other polymer sequences using, for example, light-directed synthesis techniques. See also, Fodor et. al., *Science* (1991) 251:767–777, also incorporated herein by reference for all purposes.

These techniques have met with substantial success. However, in some cases it is desirable to have alternate/additional methods of forming polymer sequences which would not utilize, for example, light as an activator, or which would not utilize light exclusively.

SUMMARY OF THE INVENTION

Methods and devices for synthesizing arrays of diverse polymer sequences such as diverse peptides and oligonucleotides are provided by virtue of the present invention. According to a preferred embodiment of the invention, a series of channels or grooves are formed on or adjacent a substrate. Reagents are selectively flowed through or placed in the channels or grooves, forming polymers having different monomer sequences at selected locations on the substrate.

According to the first specific aspect of the invention, a block having a series of grooves on a surface thereof is utilized. The block is placed in contact with a derivatized glass or other substrate. In a first step, a pipettor or other delivery system is used to flow selected reagents to one or more of a series of apertures connected to the grooves, or place reagents In the grooves directly, filling the grooves and "striping" the substrate with a first reagent, coupling a first monomer thereto. The grooves may in some embodiments thereafter be provided with additional reagents, providing coupling of additional monomers to the first monomer. The block is then translated or rotated, again placed on the substrate, and the process is repeated with a second reagent, coupling a second monomer to different regions of the substrate. The process is repeated until a diverse set of polymers of desired sequence and length is formed on the substrate. By virtue of the process, a number of polymers having diverse monomer sequences such as peptides or oligonucleotides are formed on the substrate at known locations.

According to the second aspect of the invention, a series of microchannels or microgrooves are formed on a substrate, along with an appropriate array of microvalves. The channels and valves are used to flow selected reagents over a derivatized surface. The microvalves are used to determine which of the channels are opened for any particular coupling step.

Accordingly, one embodiment of the invention provides a method of forming diverse polymer sequences on a single substrate, the substrate comprising a surface with a plurality of selected regions. The method includes the steps of forming a plurality of channels adjacent the surface, the channels at least partially having a wall thereof defined by a portion of the selected regions; and placing selected reagents in the channels to synthesize polymer sequences at the portion of the selected regions, the portion of the selected regions comprising polymers with a sequence of monomers different from polymers in at least one other of the selected regions.

A further understanding of the nature and advantages of the inventions herein may be realized by reference to the remaining portions of the specification and the attached drawings.

DESCRIPTION OF THE PREFERRED EMBODIMENTS

Contents

I. Glossary
II. General
III. Details of a First Embodiment
IV. Details of a Second Embodiment
V. Alternative Embodiments
VI. Examples
 A. Leak Testing
 B. Formation of YGGFL
VII. Conclusion

I. Glossary

The following terms are intended to have the following general meanings as they are used herein:

1. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., steroids, etc.), hormone receptors, peptides, enzymes, enzyme substrates, cofactors, drugs, (e.g., opiates, etc), lectins, sugars, oligonucleotides, nucleic acids, oligosaccharides, proteins, and monoclonal antibodies.

2. Monomer: A member of the set of small molecules which are or can be joined together to form a polymer. The set of monomers includes but is not restricted to, for example, the set of common L-amino acids, the set of D-amino acids, the set of synthetic and/or natural amino acids, the set of nucleotides and the set of pentoses and hexoses. The particular ordering of monomers within a polymer is referred to herein as the "sequence" of the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either $\alpha$-, $\gamma$-, or $\gamma$-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in copending U.S. application Ser. No. 07/796,727, filed on the same date as the present application, entitled "POLYMER REVERSAL ON SOLID SURFACES," incorporated herein by reference for all purposes.

3. Peptide: A polymer in which the monomers are alpha amino acids and which are joined together through amide bonds, alternatively referred to as a polypeptide. In the context of this specification it should be appreciated that the amino acids may be the L-optical isomer or the D-optical isomer. Peptides are often two or more amino acid monomers long, and often more than 20 amino acid monomers long. Standard abbreviations for amino acids are used (e.g., P for proline). These abbreviations are included in Stryer, Biochemistry, Third Ed., 1988, which is incorporated herein by reference for all purposes.

4. Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.

Specific examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or lead to the development of related diagnostic agents or compounds useful in therapeutic treatments such as for autoimmune immune diseases (e.g., by blocking the binding of the "self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: For instance, on compass the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

5. Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

6. Channel Block: A material having a plurality of grooves or recessed regions on a surface thereof. The grooves or recessed regions may take on a variety of geometric configurations, including but not limited to stripes, circles, serpentine paths, or the like.

7. Protective Group: A material which is bound to a monomer unit and which may be selectively removed therefrom to expose an active site such as, in the specific example of an amino acid, an amine group. Predefined Region: A predefined region is a localized area on a substrate which is, was, or is intended to be used for formation of a selected polymer and is otherwise referred to herein in the alternative as a "selected" region or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 cm$^2$, more preferably less than 1 mm$^2$, still more preferably less than 0.5 mm$^2$, and in some embodiments about 0.125 to 0.5 mm$^2$. In most preferred embodiments the regions have an area less than about 10,000 $\mu$m$^2$ or, more preferably, less than 100 $\mu$m$^2$. Within these regions, the polymer synthesized therein is preferably synthesized in a substantially pure form.

9. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is 5% pure, more preferably more than 10% pure, preferably more than 20% pure, more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

II. General

The present invention provides for the synthesis of arrays of large numbers of different polymer sequences. According to a preferred embodiment of the invention, the invention provides for the synthesis of an array of different peptides in selected regions of a substrate. Such substrates having the diverse sequences formed thereon may be used in, for example, screening studies to evaluate their interaction with receptors such as antibodies. For example, in preferred embodiments the invention provides for screening of peptides to determine which if any of a diverse set of peptides has strong binding affinity with a receptor and, in most preferred embodiments to determine the relative binding affinity of various peptides with a receptor of interest such as an antibody.

Such diverse polymer sequences are preferably synthesized on a single substrate. By synthesizing the diverse polymer sequences on a single substrate, processing of the sequences to evaluate their characteristics, such as relative binding affinity, is more easily conducted. By way of example, when a variety of peptide sequences are to be evaluated to determine their relative binding affinity to a receptor, the entire substrate and, therefore, all or a group of the polymer sequences may be exposed to an appropriately labelled receptor and evaluated simultaneously.

The diverse polymer sequences are synthesized at selected regions of a substrate by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or part of the channels, or by washing the entire substrate with appropriate reagents. After placement of a channel block on the surface of the substrate, a reagent having the monomer A flows through or is placed in all or a part of the channel(s). The channels provide fluid contact to the first selected regions, thereby binding the monomer A on the substrate directly or indirectly (via a linker) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

Various embodiments of the invention will provide for other methods of forming channels or otherwise protecting a portion of the surface of the substrate. For example, according to some embodiments a protective coating such as a hydropholic coating is utilized over portions of the substrate to be protected. Sometimes in combination with the use of various wetting materials and the like in other regions.

Figure 1:
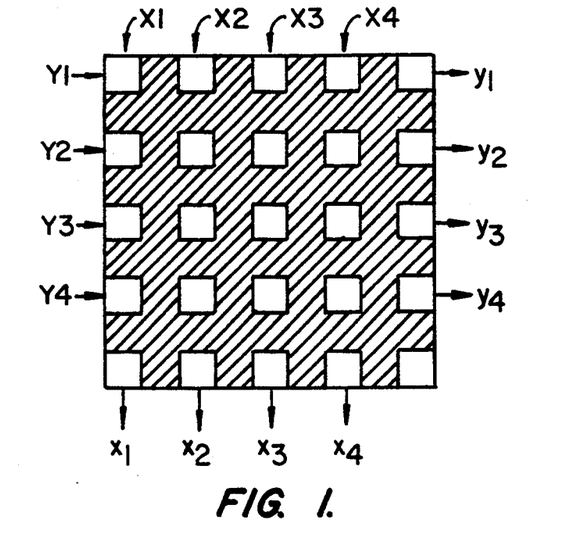
FIG. 1 is a generalized diagram illustrating the invention.

FIG. 1 illustrates an example of the invention. In this particular example, monomers and dimers of the monomer group A, B, C, and D are to be bound at selected regions of the substrate. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is preferably flat but may take on a variety of alternative surface configurations. For example, the substrate may contain raised or depressed regions on which the synthesis takes place.

The substrate and its surface form a support on which to carry out the reactions described herein. These monomers are bound using first flow channel paths $x_1$, $x_2$, $x_3$, and $x_4$ which are formed or placed on or adjacent the substrate in a first orientation, and second flow channel paths $y_1$, $y_2$, $y_3$, and $y_4$ which are formed or placed on or adjacent the substrate in a second orientation. The second flow channel paths intersect at least a part of the first flow channel paths. The flow channels are formed according to techniques which are described in greater detail elsewhere herein.

Initially the substrate is subjected to one or more preliminary treatments such as, for example, cleaning and the optional placement of "linker" molecules on the surface thereof. The substrate may also be provided with various active groups, common monomer sequences which will form a part of the polymers, or the like.

Thereafter, in a first coupling step, one or more of the flow channels are provided with the first monomer A, which binds through covalent bonds or otherwise to the substrate (directly or indirectly) where the flow channel contacts the substrate. In the particular example shown in FIG. 1, the flow channels $x_1$ and $x_2$ are utilized, binding the monomer A to the substrate along the entire length of the substrate adjacent to the $x_1$ and $x_2$ channels. It will be understood that each coupling step may in some embodiments be composed of a variety of substeps. For example, each coupling step may include one or more substeps for washing, chemical activation, or the like.

Figure 2:
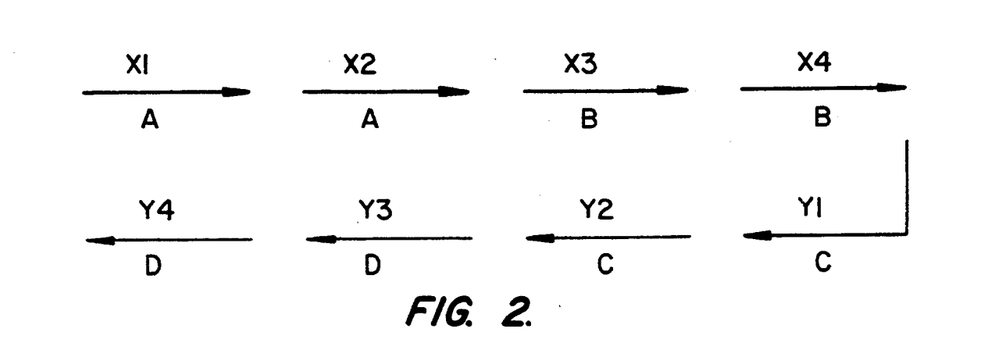
FIG. 2 is a flow chart illustrating the treatment steps performed in synthesizing an array of various polymers.

Thereafter or concurrently therewith, as shown in FIG. 2, a second monomer B is provided to selected flow channels and the monomer B binds to the substrate where the second flow channels provide contact therewith. In the particular example shown in FIG. 2, monomer B is bound along channels $x_3$ and $x_4$. When the monomers A and B flow through their respective flow channels simultaneously, only a single process step is required to perform two coupling steps simultaneously. As used herein, a "process step" refers to the injection of one or more channels with one or more reagents. A "coupling step" refers to the addition of a monomer in a polymer.

Processing thereafter continues in a similar manner with monomers C and D in the manner shown in the flow diagram of FIG. 2, with monomer C being bound in the flow channels $y_1$ and $y_2$, and D being bound in the flow channels $y_3$ and $y_4$. Preferably, monomers C and D are directed through the flow channels $y_1$ to $y_4$ simultaneously whereby two coupling steps are performed with a single process step. Light regions in FIG. 1 indicate the intersections of the resulting flow paths.

Figure 3:
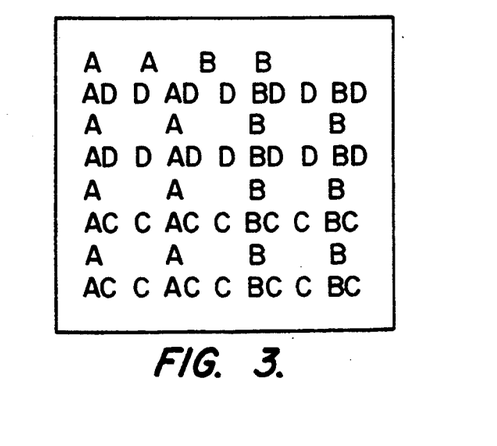
FIG. 3 is a mapping of a resulting array of polymers.

FIG. 3 illustrates the mapping of sequences formed using the above illustrated steps. As shown therein, the sequences A, B, C, D, AD, BD, AC, and BC have been formed using only two process steps. Accordingly, it is seen that the process provides for the synthesis of vast arrays of polymer sequences using only a relatively few process steps. By way of further example, it is necessary to use only two process steps to form all of the $4^2 = 16$ dimers of a four-monomer basis set. By way of further example, to form all $4^8$ octomers of a four-monomer basis set, it is necessary to provide only 256 flow channels oriented in the "x" direction, and 256 flow channels oriented in the "y" direction, with a total of eight coupling steps. Accordingly, it is seen that the present invention provides a highly efficient method of performing synthesis of diverse polymers.

III. Details of a First Embodiment

Figure 4A:
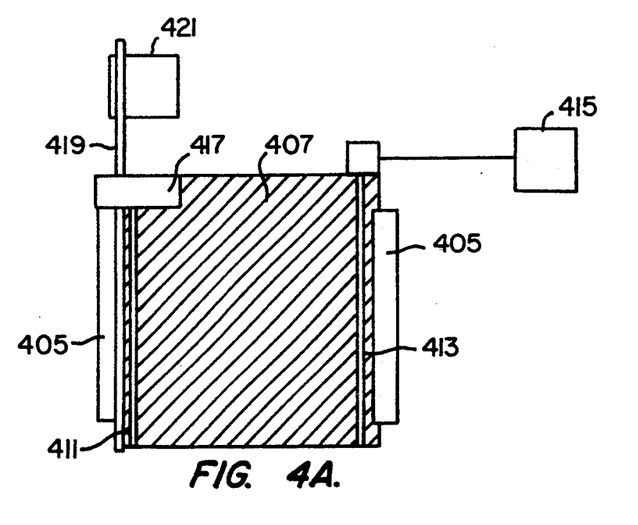
FIG. 4a is a top view and FIG. 4b is a cross-sectional view of a first embodiment of a device used to synthesize arrays of polymer sequences.
Figure 4B:
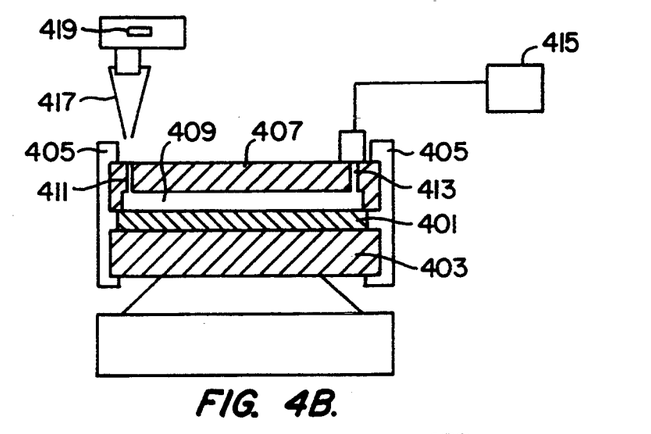

FIGS. 4a and 4b illustrate details of a first embodiment of a device used for performing the synthesis steps described above. In particular, FIG. 4a illustrates the device in top view, while FIG. 4b illustrates the device in cross-sectional side view. In the particular embodiment shown in FIG. 4, the device is used to synthesize polymer sequences on substrate 401. Substrate 401 is coupled to a rotating stage 403 and removably held by clamp 405 to channel block 407. Channel block 407 has etched therein a plurality of channels 409 in the form of stripes therein. Each channel is provided with a flow inlet 411 and an outlet 413. A vacuum source 415 is applied to one or more of the outlets 413, while a pipettor 417 is slidably mounted on arm 419 to deliver selected reagents from reservoir(s) 421 to a selected one of the flow inlets 411.

It will be recognized that in some embodiments the channel block will not be utilized. Instead, in some embodiments, small "strips" of reagent are applied to the substrate by, for example, striping the substrate or channels therein with a pipettor. According to other embodiments the channels will be formed by depositing an electron or photoresist such as those used extensively in the semiconductor industry. Such materials include polymethyl methacrylate (PMMA) and its derivatives, and electron beam resists such as poly(olefin sulfones) and the like (more fully described in Ghandi, "VLSI Fabrication Principles," Wiley (1983) Chapter 10, incorporated herein by reference in its entirety for purposes). According to these embodiments, a resist is deposited, selectively exposed, and etched, leaving a portion of the substrate exposed for coupling. These steps of depositing resist, selectively removing resist and monomer coupling are repeated to form polymers of desired sequence at desired locations.

In preferred embodiments, the substrate is conventional glass, pyrex, quartz, any one of a variety of polymeric materials, or the like. Of course, the substrate may be made from any one of a variety of materials such as silicon, polystyrene, polycarbonate, or the like. In preferred embodiments the channel block is made of polychlorotrifluorethylene, such as material known under the trade name Kel-F ® 80 (Chlorotrifluoroethylenevinylidene Fluoride) made by 3M, although a wide variety of materials such as silicon, polystyrene, polycarbonate, glass, elastomers such as Kalrez made by DuPont, various ceramics, stainless steel, or the like may be utilized.

The channels in the channel block are preferably made by machining, compression molding, injection molding, lithography, laser cutting, or the like depending upon the material of interest. In preferred embodiments the raised portions of the channels in the channel block are treated by lapping with lapping film (0.3 μm grit). Such smooth surfaces provide good seals to the substrate without the use of a sealant and, therefore, without the possibility of leaving sealant material on the substrate when rotating the channel block. Preferably, all operations are conducted at substantially ambient temperatures and pressures.

In operation, the surface of the substrate is appropriately treated by cleaning with, for example, organic solvents, methylene chloride, dimethylformamide (DMF), ethyl alcohol, or the like. Optionally, the substrate may be provided with appropriate linker molecules on the surface thereof. The linker molecules may be, for example, aryl acetylene, ethylene glycol oligomers containing from 2–10 monomers or more, diamines, diacids, amino acids, or combinations thereof. Thereafter, the surface is provided with protected surface active groups such as t-butyloxycarbonyl (TBOC) or fluoroenylmethyloycarbonyl (FMOC) protected amino acids. Such techniques are well known to those of skill in the art.

Thereafter, the channel block and the substrate are brought into contact forming fluid-tight channels bounded by the grooves in the channel block and the substrate. When the channel block and the substrate are in contact, a protective group removal agent is, thereafter, directed through a first selected channel or group of channels by placing the pipettor on the flow inlet of the selected channel and, optionally, the vacuum source on the outlet of the channel. In the case of, for example, TBOC protected amino acids, this protective group removal agent may be, for example, trifluoroacetic acid (TFA). This step is optionally followed by steps of washing to remove excess TFA with, for example, dichloromethane (DCM).

Thereafter, a first amino acid or other monomer A is directed through the first selected flow channel. Preferably this first amino acid is also provided with an appropriate protective group such as TBOC, FMOC, nitroveratryloxycarbonyl (NVOC) or the like. This step is also followed by appropriate washing steps. These steps of deprotection/coupling are concurrently with or thereafter repeated for additional channels parallel to the first channel(s) which are to be provided with the same or different monomers.

Thereafter, the substrate and the channel block are separated and, optionally, the entire substrate is washed with an appropriate material to remove any unwanted materials from the points where the channels contact the substrate.

The substrate and/or block is then, optionally, washed and translated and/or rotated with the stage. In preferred embodiments, the substrate is rotated 90 degrees from its original position, although some embodiments may provide for greater or less rotation, such as from 0 to 180 degrees. When the channel block is rotated, it may simultaneously be translated with respect to the substrate. By "translated" it is intended to mean any relative motion of the substrate and/or channel block, while "rotation" is intended to refer to rotation of the substrate and/or channel block about an axis perpendicular to the substrate and/or channel block. According to some embodiments the relative rotation is at different angles for different stages of the synthesis.

The steps of deprotection, and coupling of amino acids or other monomers is then repeated, resulting in the formation of an array of polymers on the surface of the substrate. For example, a monomer B may be directed through selected flow channels, providing the polymer AB at intersections of the channels formed by the channel block in the first position with the channels formed by the channel block after 90-degree rotation.

It will be recognized that while rotation of the channel block is provided according to preferred embodiments of the invention, such rotation is not required. For example, by simply flowing different reagents through the channels, polymers having different monomer sequences may be formed. Merely by way of a specific example, a portion of the channels may be filled with monomer "A," and a portion filled with monomer "B" in a first coupling step. All or a portion of the first channels are then filled with a monomer "C," and all or a portion of the second channels are filled with a monomer "D," forming the sequences AB and CD. Such steps could be used to form 100 sequences using a basis set of 10 monomers with a 100-groove channel block.

Figures 5A, 5B:
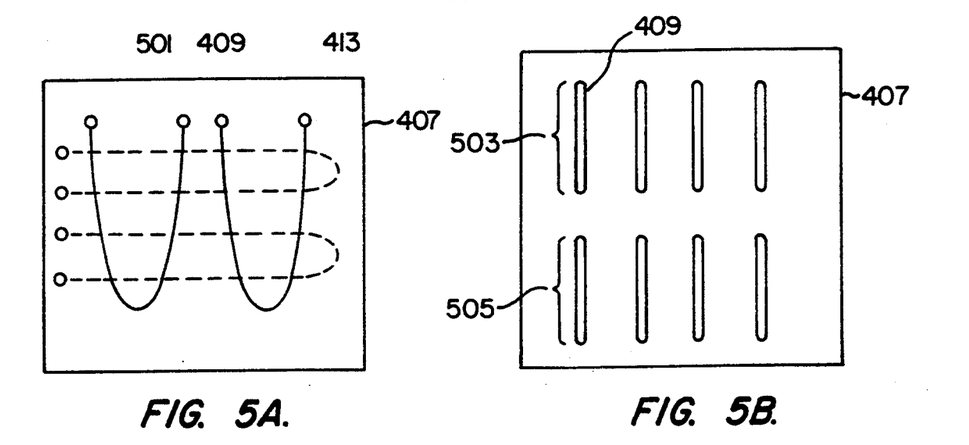
FIGS. 5a and 5b illustrate alternative arrangements of the grooves in a channel block.

While linear grooves are shown herein in the preferred aspects of the invention, other embodiments of the invention will provide for circular rings or other shapes such as circular rings with radial grooves running between selected rings. According to some embodiments, channel blocks with different geometric configurations will be used from one step to the next, such as circular rings in one step and linear stripes in the next. FIG. 5a illustrates one of the possible arrangements in which the channels 409 are arranged in a serpentine arrangement in the channel block 407. Through appropriate translation and/or rotation of the channel block, polymers of desired monomer sequence are formed at the intersection of the channels during successive polymer additions, such as at location 501, where the intersection of a previous or subsequent set of channels is shown in dashed lines. FIG. 5b illustrates another arrangement in which channels (in this case without flow paths 413) are provided in a linear arrangement, with groups 503 and 505 located in adjacent regions of the substrate and extending only a portion of the substrate length.

In some embodiments of the invention, the various reagents, such as those containing the various monomers, are not pumped through the flowpaths 413. Instead, the reagent is placed in one of the grooves, such as the grooves 409 shown in FIG. 5b, filling the groove. The substrate is then placed on top of the channel block, and the exposed portions of the substrate are permitted to react with the materials in the grooves. In preferred embodiments, the channels are of the same width as the raised regions between the channels. According to these embodiments, the substrate may then be moved laterally by one channel width or an integer multiple of a channel width, permitting reaction with and placement of monomers on the regions between the channels in a previous coupling step. Thereafter, the substrate or channel block will be rotated for the next series of coupling steps.

Through avoidance of the placement of substantial pressure on the substrate by the channel block in this manner, damage to these intervening regions may be avoided. Also, such methods will be resistant to problems created by "dead spots" in the flow channels when reagents are pumped through the channels. According to these embodiments, the array of synthesized polymers can easily cover the entire substrate. Such embodiments may simultaneously couple up to, e.g., 20 peptides in a single step.

In preferred embodiments, the process is repeated to provide more than 10 different polymer sequences on the surface of the substrate. In more preferred embodiments, the process is repeated to provide more than $10^2$, $10^3$, $10^4$, $10^5$, or more polymer sequences on a single substrate. In some embodiments the process is repeated to provide polymers with as few as two monomers, although the process may be readily adapted to form polymers having 3, 4, 5, 6, 10, 15, 20, 30, 40, 50, 75, 100 or more monomers therein.

According to preferred embodiments, the array of polymer sequences is utilized in one or more of a variety of screening processes, one of which is described in copending U.S. application Ser. No. 07/796,947, filed on the same day as the present application and incorporated herein by reference for all purposes. For example, according to one embodiment, the substrate is then exposed to a receptor of interest such as an enzyme or antibody. According to preferred embodiments, the receptor is labelled with fluorescein, or otherwise labelled, so as to provide for easy detection of the location at which the receptor binds. According to some embodiments, the channel block is used to direct solutions containing a receptor over a synthesized array of polymers. For example, according to some embodiments the channel block is used to direct receptor solutions having different receptor concentrations over regions of the substrate.

According to most preferred embodiments, amplification of the signal provided by way of fluorescein labelling is provided by exposing the substrate to the antibody of interest, and then exposing the substrate to a labelled material which is complementary to the antibody of interest and preferably binds at multiple locations of the antibody of interest. For example, in one specific embodiment, if a mouse antibody is to be studied, a labelled second antibody may be exposed to the substrate which is, for example, goat antimouse. Such techniques are described in copending U.S. application Ser. No. 07/624,120, previously incorporated herein by reference.

IV. Details of a Second Embodiment

According to some embodiments of the invention, microvalve structures are used to form channels along selected flow paths on the substrate. According to these embodiments, an array of microvalves are formed and operated by an overlying or underlying array of electrodes which are used to energize selected valves to open and close such valves.

Figure 6A:
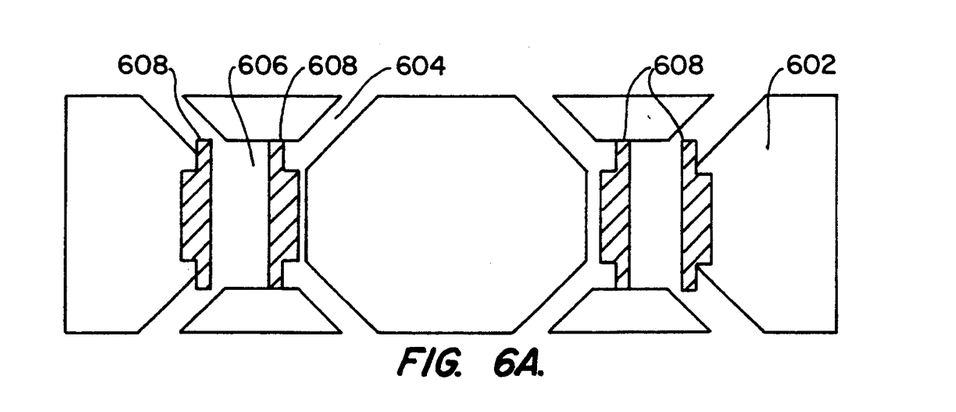
FIGS. 6a and 6b illustrate a microvalve device.
Figure 6B:
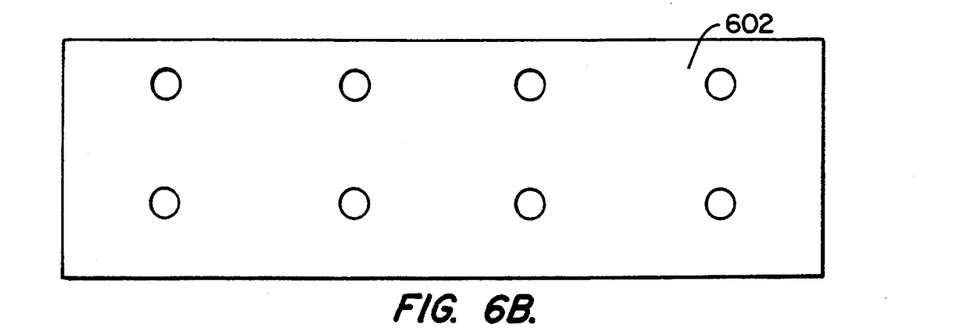

FIG. 6 illustrates such a structure, FIG. 6a illustrating the system in end view cross-section and FIG. 6b illustrating the system in top view. It will be recognized that the structure shown therein provides for only two synthesis chambers for the purpose of clarity, but in most embodiments a far greater number of chambers will be provided. Microvalves are discussed in detail in, for example, Zdeblick, U.S. Pat. No. 4,966,646, and Knutti, "Advanced Silicon Microstructures," ASICT Conference (1989), both incorporated herein by reference for all purposes.

As shown therein, a substrate 602 is provided with a plurality of channels 604 formed using photolithographic, or other related techniques. The channels lead up to a synthesis chamber 606. At the end of each channel is valve structure 608. As shown in FIG. 6, the channels lead up to the chambers, but may be isolated from the chambers by the valves. Multiple valves may be provided for each chamber. In the particular structure shown in FIG. 6, the right valve on the left chamber and the left valve on the right chamber are open while the remaining valves are closed. Accordingly, if reagent is delivered to the top of the substrate, it will flow through the open channel to and through the chamber on the left, but not the one on the right. Accordingly, coupling steps may be conducted on the chamber with selected reagents directed to selected chambers, using the techniques discussed above.

According to some embodiments, a valve is supplied on one side of the chamber 606, but the valve on the opposite side is replaced by a semi-permeable membrane. According to these embodiments it becomes possible to flow a selected reagent into the chamber 606 and, thereafter, flow another selected reagent through the flow channel adjacent the semi-permeable membrane. The semi-permeable membrane will permit a portion of the material on one side or the other to pass through the membrane. Such embodiments will be useful in, for example, cell studies.

Screening will be performed by, for example, separating or cutting two halves of the device, enabling screening by, for example, contacting with a fluorescein labelled antibody, or the like followed by photodetection.

V. Alternative. Embodiments

Figure 7A:
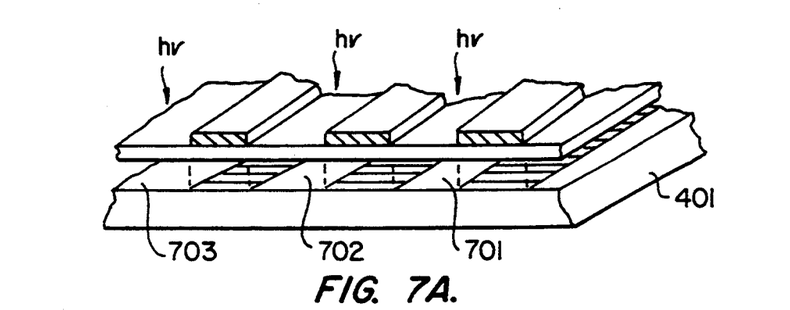
FIGS. 7a and 7b illustrate an alternative embodiment of the invention.
Figure 7B:
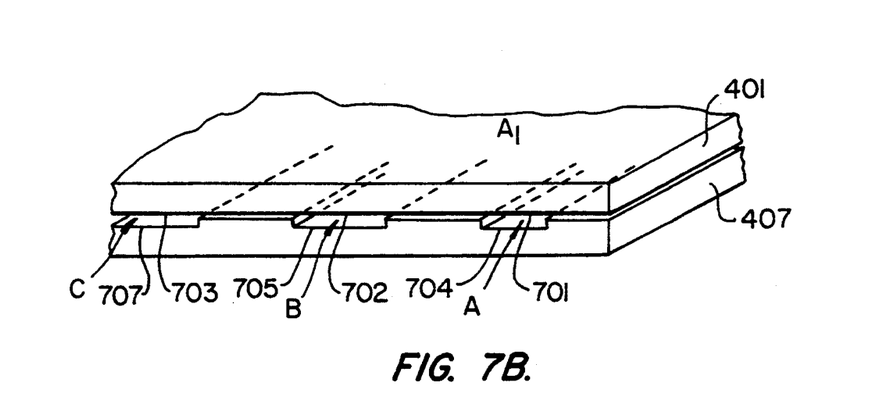

FIGS. 7a and 7b illustrate one alternative embodiment of the invention which combines the mechanical polymer synthesis techniques disclosed herein with light-directed synthesis techniques. According to these embodiments, a substrate 401 is irradiated in selected regions, shown as the non-striped regions in FIG. 7a. The surface of the substrate is provided with photoremovable groups in accordance with copending U.S. application Ser. No. 07/624,120, previously incorporated by reference, on, for example, amine groups in the specific case of peptide synthesis. During this step regions 701, 702, and 703 of the substrate, among others, are deprotected, leaving remaining regions of the substrate protected by photoremovable groups such as NVOC. According to a specific embodiment of the invention the widths of the irradiated regions equal the widths of the protected regions of the substrate.

Thereafter, as shown in FIG. 7b the substrate is contacted with a channel block 407. In the particular embodiment shown in FIG. 7b, the channels 704, 705, and 707 are aligned with the regions 701, 702, and 703, respectively, on the substrate 401. As will be apparent, specific embodiments of the invention provide for irradiated regions and channels in the form of stripes, which are aligned during this step. Other embodiments, however, will provide for other shapes of irradiated regions and channels, and other relative orientations of the irradiated regions and channels. The channel block and substrate will be aligned with, for example, an alignment mark placed on both the substrate and the channel block. The substrate may be placed on the channel block with, for example, a vacuum tip.

Thereafter, a selected reagent is flowed through or placed in the channels in the channel block for coupling to the regions which have previously been exposed to light. As with the first embodiment, the substrate may be placed in contact with a prefilled channel block in some embodiments to avoid compression of the channel block to the substrate and dead spots during pumping. According to preferred aspects of the invention, a different reagent flows through each of the channels 701, 702, and 703 such as, for example, a reagent containing monomers A, B, and C. The process may then, optionally, involve a second coupling step in which the substrate is translated by, e.g., one channel width, to provide coupling of a monomer in the regions between the original channels.

Thereafter, the process of directed irradiation by light, followed by coupling with the channel block is repeated at the previously unexposed regions. The process is then preferably repeated again, with the stripes of the mask and the channel block rotated at, for example, 90 degrees. The coupling steps will provide for the formation of polymers having diverse monomer sequences at selected regions of the substrate through appropriate translation of the mask and substrate, and through appropriate mask selection.

It is seen that through a combination of the light-directed techniques and the mechanical flow channel techniques disclosed herein, greater efficiency in forming diverse sequences is achieved since multiple monomers are coupled in a single irradiation/coupling step.

VI. Examples

A. Leak Testing

An initial experiment was conducted using the device described in the first embodiment to assure that materials could be delivered to selected locations of a substrate and be prevented from contacting other areas. Additionally, the experiment was used to demonstrate that reagents could be delivered in a uniform manner.

Accordingly, a flat piece of conventional glass having dimensions of about 42 mm×42 mm was derivatized with aminopropyltriethoxysilane. The entire slide was deprotected and washed using conventional techniques. A fluorescein marker of fluoroescinisothiocyanate (FITC) was then injected into flow channels formed when a block of KelF ® 81 with 10 channels of 1 mm depth and 1 mm width were brought into contact with the substrate. The fluorescein marker was in a solution of DMF and flowed through the channels by injecting the material into the groove with a manual pipet.

Figure 8:
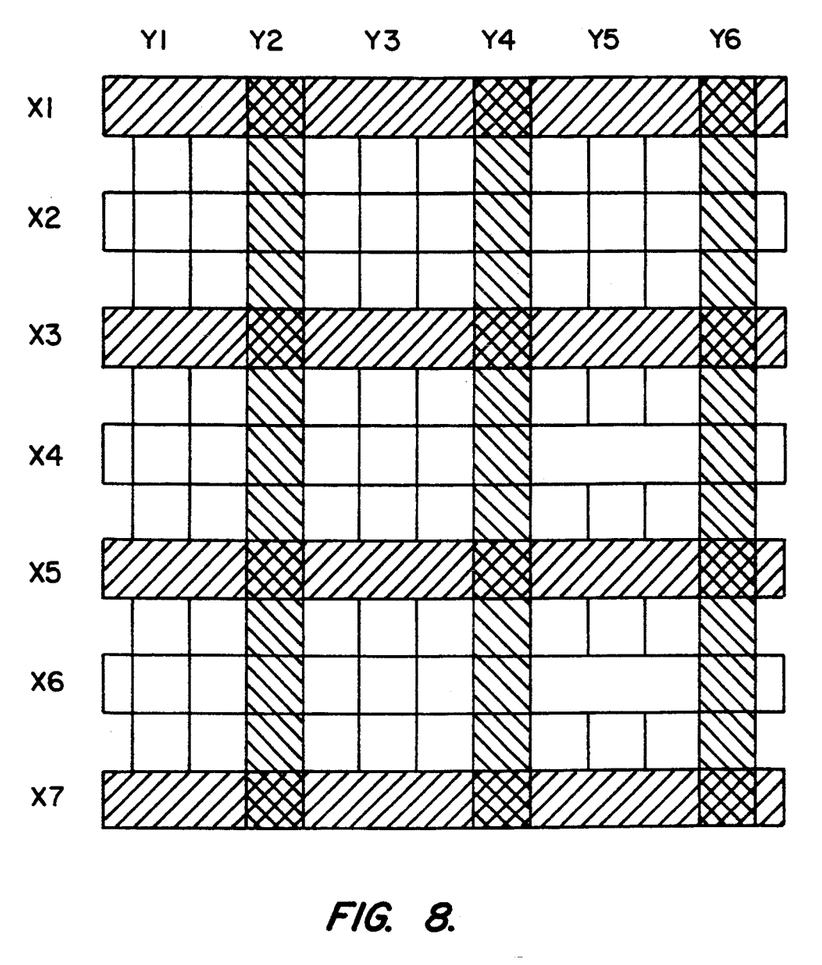
FIG. 8 is a mapping of expected fluorescent intensities with a substrate selectively exposed to fluorescent dye.

Fluorescein dye was similarly injected into every other channel in the block, the block was rotated, and the process was repeated. The expected resulting plot of fluorescent intensity versus location is schematically illustrated in FIG. 8. Dark regions are shown at the intersections of the vertical and horizontal stripes, while lighter grey at non-intersecting regions of the stripes. The dark grey regions indicate expected regions of high dye concentration, while the light regions indicate regions of expected lower dye concentration.

Figure 9:
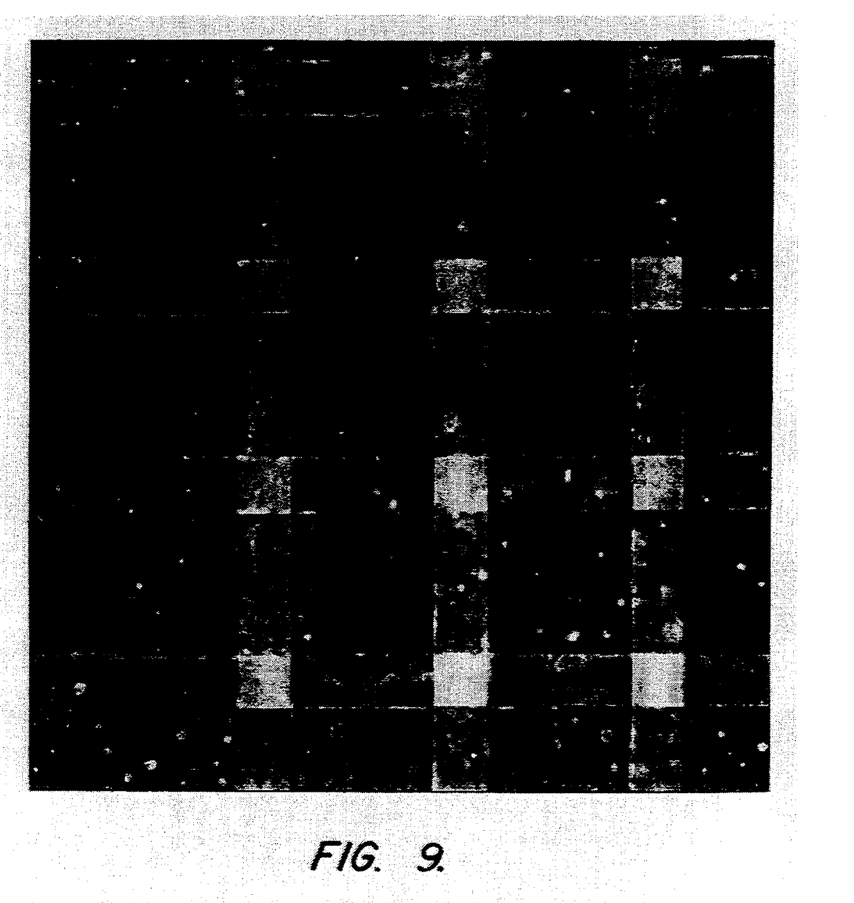
FIG. 9 is a mapping of actual fluorescent intensities.

FIG. 9 is a mapping of fluorescence intensity of a portion of an actual slide, with intensity data gathered according to the methods of copending U.S. application Ser. No. 07/624,120, previously incorporated by reference. The results agree closely with the expected results, exhibiting high fluorescence intensity at the intersection of the channels (about 50% higher than non-intersecting regions of the stripes), and lower fluorescence intensity at other regions of the channels. Regions which were not exposed to fluorescence dye show little activity, indicating a good signal-to-noise ratio. Intersections have fluorescence intensity about 9x as high as background. Also, regions within the channels show low variation in fluorescence intensity, indicating that the regions are being evenly treated within the channels.

B. Formation of YGGFL

The system was used to synthesize four distinct compounds: YGGFL (SEQ. ID NO:1), YpGFL (SEQ ID NO:2), pGGFL (SEQ ID NO:3), and ppGFL. An entire glass substrate was derivatized with TBOC-protected aminopropyltriethoxysilane, deprotected with TFA, coated with FMOC-protected caproic acid (a linker), deprotected with piperidine, and coated with FMOC-protected Glycine-Phenylalanine-Leucine (GFL).

This FMOC-GFL-coated slide was sealed to the channel block, and all 10 grooves were deprotected with piperidine in DMF. After washing the grooves, FMOC Glycine (G) was injected in the odd grooves, and FMOC d-Proline (p) was injected in the even grooves. After a two-hour coupling time, using standard coupling chemistry, all grooves were washed with DMF. The grooves were vacuum dried, the block removed and rotated 90 degrees. After resealing, all grooves were deprotected with piperidine in DMF and washed. FMOC Tyrosine (Y) was injected in the odd grooves, and FMOC p in the even grooves. After coupling the grooves were washed and vacuum dried. Accordingly, 25 regions of each of the compounds YGGFL, YpGFL, pGGFL, and ppGFL were synthesized on the substrate. The substrate was removed and stained with FITC-labelled antibodies (Herz antibody 3E7).

Figure 10:
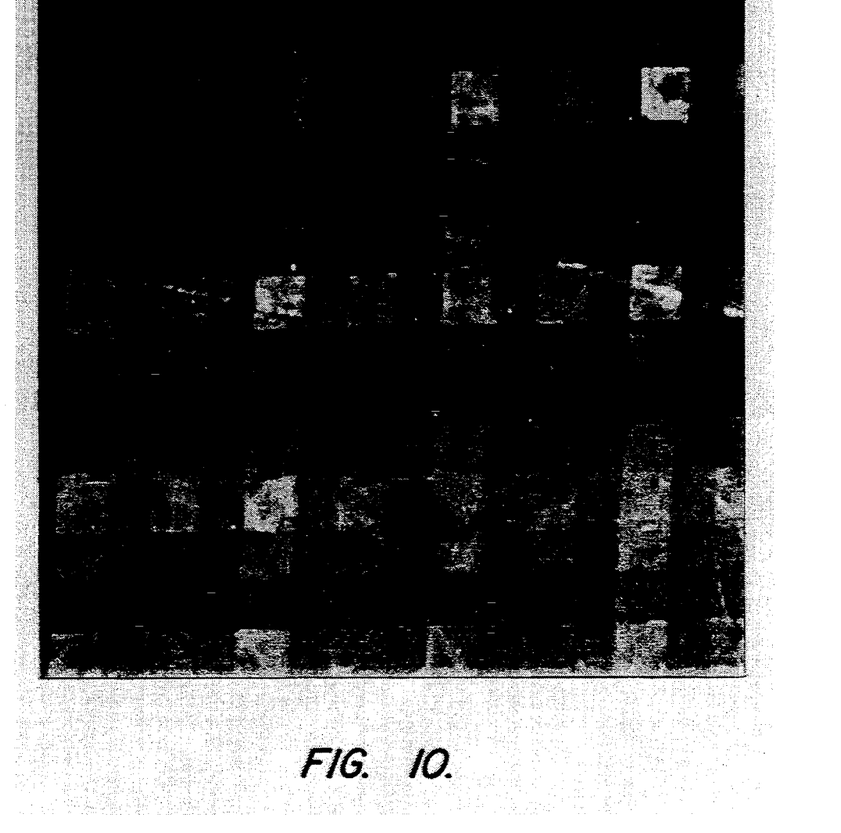
FIG. 10 is a mapping of intensity versus location with a slide having YGGFL, GpGFL, pGGFL, and pPGFL synthesized thereon.

A section of the resulting slide illustrating fluorescence intensity is shown in FIG. 10. White squares are in locations of YGGFL. The darkest regions are pGGFL and ppGFL. The YGGFL sites were the most intense, followed by the YpGFL sites. The pGGFL and ppGFL intensities were near background levels, consistent with expected results with the Herz antibody.

Quantitative analysis of the results show overall intensity ratios for YGGFL:YpGFL:pGGFL:ppGFL as 1.7:1.5:1.1:1.0. However, since there is a large standard deviation on the YGGFL and YpGFL, comparing all the sites with each other may not accurately represent the actual contrasts. Comparing the intensities of sites within the same "stripe" gives larger contrasts, although they remain on the order of 2:1.

VII. Conclusion

The above description is illustrative and not restrictive. Many variations of the invention will become apparent to those of skill in the art upon review of this disclosure. Merely by way of example a variety of substrates, receptors, ligands, and other materials may be used without departing from the scope of the invention. The scope of the invention should, therefore, be determined not with reference to the above description, but instead should be determined with reference to the appended claims along with their full scope of equivalents.

What is claimed is:

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

Tyr  Gly  Gly  Phe  Leu
    1                         5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

Tyr  Gly  Phe  Leu
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

Gly  Gly  Phe  Leu
    1

1. A method of forming a plurality of peptide sequences on a surface of a single substrate comprising the steps of:
   a) contacting said substrate with a channel block in a first orientation, said channel block comprising a substantially planar member with a plurality of recessed regions and raised walls on a surface thereof, said recessed regions forming channels, said raised walls effective to produce substantially fluid-tight seals between said raised walls and said substrate upon said contacting to define thereby a first plurality of flow channels between said channel block and said substrate, said first flow channels dividing said substrate surface into at least a first portion and a second portion;
   b) flowing at least a first amino acid through at least one of said first flow channels, and convalently coupling said first amino acid to said first portion of said substrate surface, said first amino acid comprising a reactive group protected by a protecting group;
   c) flowing at least a second amino acid through at least one of said first flow channels, and covalently coupling said second amino acid to said second portion of said substrate surface, said second amino acid comprising a reactive group protected by a protecting group;
   d) translating said channel block relative to said substrate and contacting said substrate with said channel block in a second orientation to produce substantially fluid-tight seals between said raised walls and said substrate upon said contacting to define thereby a second plurality of flow channels between said channel block and said substrate, said second flow channels dividing said substrate surface into at least a third portion and a fourth portion, said third and fourth portions each having at least one intersection with each of said first and second portions of said substrate surface;
   e) removing said protective groups from at least a portion of said first or second amino acids to form a first set of deprotected first or second amino acids and flowing a third amino acid through at least one of said second flow channels, covalently coupling said third amino acid to said third portion of said substrate surface and covalently coupling said third amino acid to at least a portion of said firs set of deprotected first or second amino acids through a peptide bond therewith where said first and second portions of said substrate surface intersect with said third portion of said substrate surface to form first and second peptide sequences; and f) removing said protective group from at least a portion of said first and second amino acids to form a second set of deprotected first or second amino acids and flowing a fourth amino acid through at least one of said second channels, covalently coupling said fourth amino acid to said fourth portion of said substrate surface and covalently coupling said fourth amino acid to at least a portion of said second set of deprotected first or second amino acids through a peptide bond therewith where said fourth portion of said substrate intersects with said first and second portions of said substrate surface to form third and fourth peptide sequences.

2. The method as recited in claim 1 wherein at least 10 different peptide sequences are formed on said surface.

3. The method as recited in claim 1 wherein at least 100 different peptide sequences are formed on said surface.

4. The method as recited in claim 1 wherein at least 1,000 different peptide sequences are formed on said surface.

5. The method as recited in claim 1 wherein at least 10,000 different peptide sequences are formed on said surface.

6. The method as recited in claim 1 wherein at least 100,000 different peptide sequences are formed on said surface.

7. The method as recited in claim 1 wherein each different peptide sequence is in a region having an area of less than about 1 cm$^2$.

8. The method as recited in claim 1 wherein each different peptide sequence is in a region having an area of less than about 1 mm$^2$.

9. The method as recited in claim 1 wherein the surface of said substrate comprises active groups capable of forming a covalent bond with amino acids, said active groups protected with photoremovable groups, and wherein the step of forming a first plurality of flow channels is preceded by a step of irradiating portions of said substrate with a light source shown through a mask whereby said photoremovable groups are removed from at least some of the active groups on said substrate surface in order for at least said first amino acid to covalently bind thereto.

10. The method as recited in claim 9 wherein each different peptide sequence is in a region having an area of less than about 10,000 microns$^2$.

11. The method as recited in claim 9 wherein said irradiated portions are in the form of stripes, and wherein said step of forming said first plurality of flow channels comprises forming said first channels along a path of said stripes, and wherein different reagents are placed in at least a portion of said flow channels, said reagents selected from the group consisting of amino acids, wash solutions and protective group removal agents.

12. The method as recited in claim 1 wherein each said step of flowing said first, second, third, or fourth amino acids through its respective said first or second flow channels comprises:

placing a pipet in fluid communication with said first or second flow channel; and injecting said first, second, third or fourth amino acid from said pipet through its respective said first or second flow channel.

13. The method as recited in claim 12 wherein said step of placing the pipet in fluid communication with said first or second flow channel includes placing said pipet in contact with an orifice on a side of said substrate.

14. The method as recited in claim 12 wherein said step of placing the pipet in fluid communication with said first or second flow channel is a step of placing a plurality of pipettes in fluid communication with a plurality of said first or second flow channels and flowing reagents selected from the group consisting of said first, second, third and fourth amino acids, wash solutions and protective group removal agents through at least two of said first or second flow channels.

* * * * *